US010297414B2

(12) United States Patent
Meiler et al.

(10) Patent No.: US 10,297,414 B2
(45) Date of Patent: May 21, 2019

(54) X-RAY TUBE DEVICES AND METHODS FOR IMAGING SYSTEMS

(71) Applicant: VAREX IMAGING CORPORATION, Salt Lake City, UT (US)

(72) Inventors: Michael Meiler, Draper, UT (US); Inwoo Yoon, South Jordan, UT (US); Christopher Lewis, Kaysville, UT (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 171 days.

(21) Appl. No.: 15/271,041

(22) Filed: Sep. 20, 2016

(65) Prior Publication Data

US 2018/0082818 A1  Mar. 22, 2018

(51) Int. Cl.

| H01J 35/02 | (2006.01) |
|---|---|
| H01J 35/06 | (2006.01) |
| H01J 35/08 | (2006.01) |
| H01J 35/14 | (2006.01) |
| A61B 6/00 | (2006.01) |
| A61B 6/03 | (2006.01) |

(52) U.S. Cl.
CPC .......... *H01J 35/025* (2013.01); *A61B 6/4494* (2013.01); *H01J 35/06* (2013.01); *H01J 35/08* (2013.01); *H01J 35/14* (2013.01); *A61B 6/032* (2013.01)

(58) Field of Classification Search
CPC .......... H01J 35/00; H01J 35/02; H01J 35/025; H01J 35/06; H01J 35/08; H01J 35/14; H01J 35/16; A61B 6/03; A61B 6/032

USPC ................. 378/207, 162, 165, 114, 121, 113
See application file for complete search history.

(56) References Cited

U.S. PATENT DOCUMENTS

| 5,550,889 A | 8/1996 | Gard et al. | |
|---|---|---|---|
| 7,120,547 B2 * | 10/2006 | Herrmann | A61B 6/56 702/85 |
| 7,766,549 B2 * | 8/2010 | Flukiger | A61B 6/00 378/101 |

OTHER PUBLICATIONS

Extended European Search Report issued in European Application No. 17191184.5, dated Feb. 15, 2018; Varex Imaging Corporation; 6 pages.

* cited by examiner

*Primary Examiner* — Jurie Yun
(74) *Attorney, Agent, or Firm* — Maschoff Brennan

(57) ABSTRACT

An X-ray tube may include a housing, a cathode, an anode, and a tube auxiliary unit or an authentication module. The cathode and the anode are positioned within the housing. The cathode and the anode are spaced apart such that a target surface of the anode is positioned to receive electrons emitted by the cathode. The tube auxiliary unit may be coupled to the housing. The tube auxiliary unit may include X-ray tube data including tube calibration data based on parameters of the X-ray tube. The authentication module may be configured to authenticate the X-ray tube with a tube control unit.

21 Claims, 8 Drawing Sheets

X-RAY TUBE DEVICES AND METHODS FOR IMAGING SYSTEMS

BACKGROUND

The present disclosure generally relates to X-ray imaging systems, including embodiments relating to the control, calibration and/or monitoring of an X-ray tube in an X-ray imaging system.

Computed tomography (CT) or X-ray imaging systems typically include an X-ray tube, a detector, and a support structure, such as a gantry, for the X-ray tube and the detector. In operation, an imaging table, on which a patient or object is positioned, is located between the X-ray tube and the detector. The X-ray tube typically emits radiation, such as X-rays, toward the object. The radiation passes through the object on the imaging table and impinges on the detector. As radiation passes through the object, internal structures of the object cause spatial variances in the radiation received at the detector. The detector receives the radiation and transmits data representative of the received radiation. The system translates the radiation variances into an image, which may be used to evaluate the internal structure of the object. The object may include, but is not limited to, a patient in a medical imaging procedure and an inanimate object in a package scanner.

The claimed subject matter is not limited to embodiments that solve any disadvantages or that operate only in environments such as those described above. This background is only provided to illustrate examples of where the present disclosure may be utilized.

SUMMARY

The present disclosure relates to an X-ray imaging system that facilitates simple and accurate updating of a calibration file to be used by a tube control unit for controlling the operation of a given X-ray tube. Embodiments also minimize or prevent use of an X-ray tube with a mismatched or incompatible control system (tube control unit). Use of the correct calibration file with a given X-ray tube serves to insure proper, reliable and safe operation of the tube specifically, and the imaging system in general. Embodiments also pertain to the collection of X-ray tube operational data that can be used to generate and forecast tube diagnostics, thereby reducing downtime of the tube and corresponding imaging system.

In one example embodiment, an X-ray tube may include a housing, a cathode, an anode, and a tube auxiliary unit. The tube auxiliary unit may be coupled to the housing, and is operably connected to a tube control unit, which may be remote from the tube auxiliary unit (such as another portion of a gantry in an imaging system). Operation of the X-ray tube may be at least partially controlled by the tube control unit. The tube auxiliary unit may include a memory device or component that is configured to store X-ray tube data, including tube calibration data that reflects predetermined operating parameters or characteristics that are, at least in part, unique to the specific X-ray tube. For example, such data might include focal spot size and focal spot position for various combinations of operating voltage and current. The X-ray tube data may also include manufacturing data pertaining to the X-ray tube. For example, such data might include one or more of tube serial number, manufacturing date, calibration tables, batch or lot number, calibration date, part number, and the like.

In another embodiment, the tube auxiliary unit may include a programmable controller, such as a microprocessor, field-programmable gate array (FPGA), or similar device or circuit. The programmable controller may be operatively connected to one or more sensors positioned on or within the X-ray tube so as to sense, detect or measure various tube operating parameters and data, including but not limited to tube operating current (mA), tube operating voltage (kV), filament current, anode speed and acceleration, gantry speed, X-ray exposure time/duration, cumulative or session operating time of components, electron beam steering patterns, coolant flow rate, temperature, tube vibration, audible noise and the like. Such operating parameters may then be used to generate diagnostic information for the X-ray tube, such as end-of-life predictions for the tube itself, and/or for individual components, such as bearings, the emitter, or the anode. The ability to forecast X-ray tube or component life may prevent expensive X-ray tube down time and loss of revenues to the user. It may also allow a user or supplier to order and replace an X-ray tube or a component prior to actual failure.

In another example, a method may include receiving X-ray tube data at a tube control unit from a tube auxiliary unit. The tube auxiliary unit may be coupled to a housing of an X-ray tube, which in turn is connected to a gantry, and the tube control unit may be coupled to a gantry or similar structure within the system. The received X-ray tube data may include tube calibration data, which may reflect unique operating parameters/characteristics of the X-ray tube of the sort, for example, noted above. The method may further include combining the received X-ray tube data with tube control unit data stored at the tube control unit, as well as with any customer adjustment data/parameters. The tube control unit data may then utilize the combined data to create, or otherwise provide a calibration file that is used by the tube control unit to operate at least some aspects of the X-ray tube, including, for example, electron beam control (e.g., electrostatic and/or magnetic focusing and magnetic steering coil settings to control the positioning and size of the electron beam and resulting focal spot provided by the X-ray tube during operation).

In another example embodiment, an X-ray tube may include a housing, a cathode, an anode, and an authentication module. The authentication module may be configured to authenticate the X-ray tube with a tube control unit, which may also be equipped with an authentication module, so as to, for example, insure a proper match between tube and control unit. In some embodiments, the authentication module(s) include features that render the module "tamper-proof," thereby preventing, or at least minimizing, the ability to circumvent the authentication function by, for example, altering or changing authentication parameters or algorithms of the authentication module(s). Authenticating the X-ray tube and the tube control unit may facilitate safe and/or proper operation of the X-ray tube.

In yet another example, a method may include confirming that an X-ray tube is properly matched to a tube control unit to establish that the two devices will interoperate correctly. The method may include, for example, exchanging one or more authentication codes, either from the X-ray tube to the tube control unit, the tube control unit to the X-ray tube, or both (two-way authentication). If the exchanged code(s) match a predetermined key, for example, or otherwise comply with a predetermined security algorithm, then it is determined that the X-ray tube and the tube control unit match. In some embodiments, only once a match is confirmed between a given X-ray tube and tube control unit, will the X-ray tube release any data to the tube control unit. In some embodiments, the authentication codes are exchanged via an encrypted communication link. In still further embodiments, authentication codes are continuously changed to prevent unauthorized detection of a code.

The disclosed X-ray imaging systems may insure that the calibration file(s) used by a tube control unit is always up-to-date and accurate for a given X-ray tube. Moreover, the process can be automatic and transparent to a user, thereby eliminating the need to manually obtain a correct calibration file for a new tube. This minimizes the mismatching of calibration files to reduce problems associated with decreased image quality, image artifacts, incorrect focal spot sizes and/or positioning, failed magnetics, X-ray tube damage (e.g., punctures, anode meltdown, aperture overheating, etc.), dosimetric errors leading to overexposure of the patient to radiation, and/or downtime of the X-ray imaging system for service and repairs and any other problems associated with use of the wrong calibration file. In addition, the disclosed X-ray imaging systems may validate X-ray tubes with functionally compatible control systems (e.g., tube control units) to avoid mismatches. Moreover, embodiments provide the ability to obtain substantially real time diagnostic information that can be used, among other things, to forecast X-ray tube or component failures and thereby avoid costly downtime.

This Summary introduces a selection of concepts in a simplified form that are further described below in the Detailed Description. This Summary is not intended to identify key features or essential characteristics of the claimed subject matter, nor is it intended to be used as an aid in determining the scope of the claimed subject matter.

DETAILED DESCRIPTION

Figure 1:
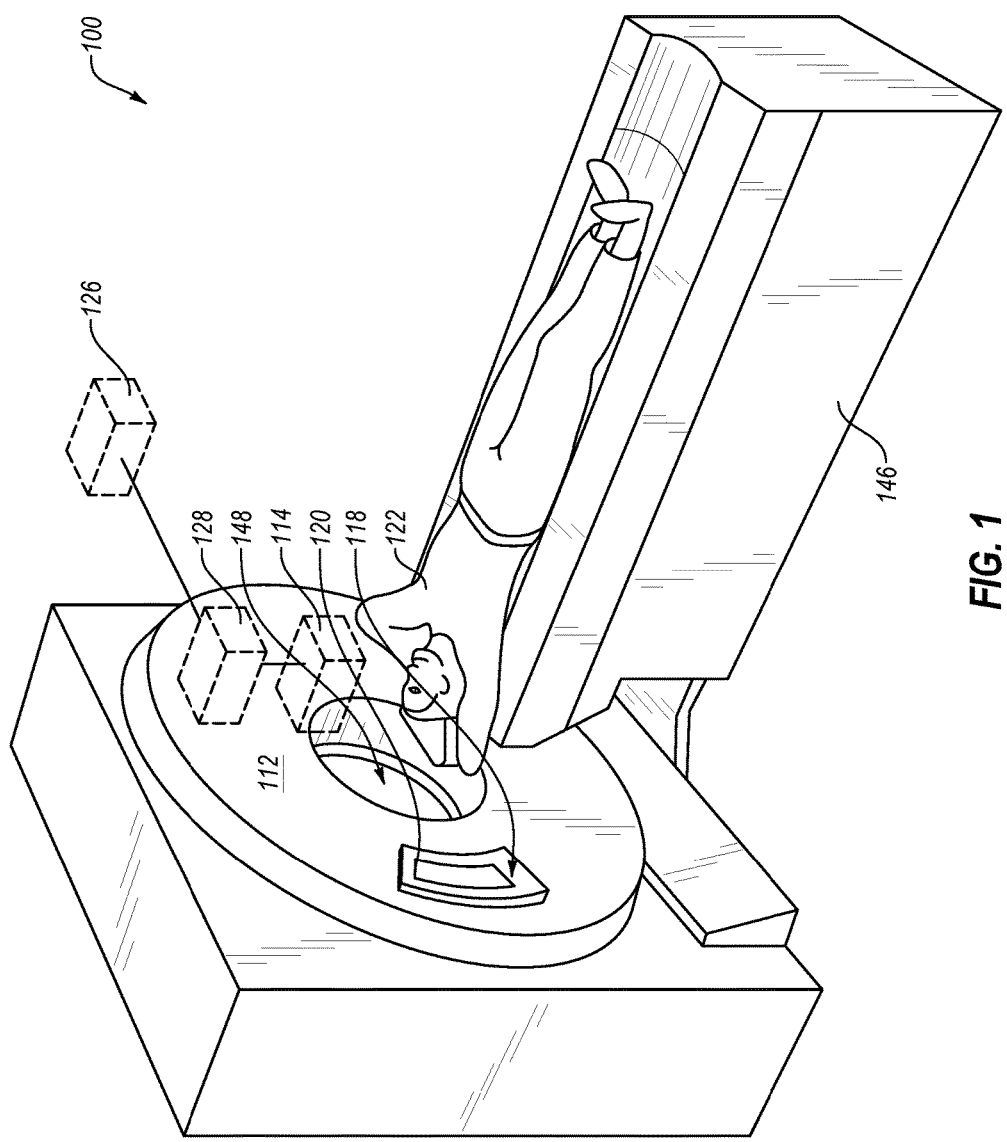
FIG. 1 is a perspective view of one example of an X-ray imaging system.

Reference will be made to the drawings and specific language will be used to describe various aspects of the disclosure. Using the drawings and description in this manner should not be construed as limiting its scope. Additional aspects may be apparent in light of the disclosure, including the claims, or may be learned by practice.

The present disclosure generally relates to X-ray imaging systems.

Computed tomography (CT) or X-ray imaging systems typically include an X-ray tube, a detector, and a support structure, such as a gantry, for the X-ray tube and the detector. In operation, an imaging table, on which a patient or object is positioned, is located between the X-ray tube and the detector. The X-ray tube typically emits radiation, such as X-rays, toward the object. The radiation passes through the object on the imaging table and impinges on the detector. As radiation passes through the object, internal structures of the object cause spatial variances in the radiation received at the detector. The detector receives the radiation and transmits data representative of the received radiation. The system translates the radiation variances into an image, which may be used to evaluate the internal structure of the object. The object may include, but is not limited to, a patient in a medical imaging procedure and an inanimate object in a package scanner.

X-ray imaging systems may include one or more control systems configured to operate components within the system, such as the X-ray tube, the detector, the gantry, the imaging table and/or other components. One example control system, sometimes referred to as a "tube control unit" or "TCU," may control the operation of an X-ray tube, including, for example, focal spot size and focal spot position by driving correct focus and steering coil settings of the X-ray tube. Since each X-ray tube may have unique operational characteristics, a tube control unit typically requires access to calibration information, sometimes referred to as a "calibration file," that includes control parameter data that is specific to a given X-ray tube. For example, focal spot sizes and focal spot positions for various combinations of tube operating voltages (kV) and tube emitter currents (mA) are unique to each X-ray tube, and thus such unique calibration data must be included within the calibration file used by a tube control unit for a given X-ray tube. The tube control unit may then apply the calibration file to its algorithms to control, for example, focusing and steering components within the X-ray tube.

The need for a unique calibration file for a given X-ray tube can give rise to a variety of problems. For example, if the X-ray tube in an X-ray imaging system is replaced or repaired, the calibration file used by the tube control unit may have to be updated, or completely replaced, to reflect the unique operating characteristics of the new or repaired X-ray tube to ensure it is properly controlled by the tube control unit. In a typical X-ray imaging system, the calibration file must be updated manually based on the unique calibration data of the X-ray tube that is to be used. This may prolong service time, and, in some circumstances, introduce errors if the calibration information is not correct or accurate for a given X-ray tube.

Moreover, if a tube control unit does not have the correct calibration information for a given tube (for example, if the calibration file is not updated, not updated properly, or is for a different tube), the incorrect information may result in the tube control unit operating the X-ray tube improperly. Improper operation can result in a number of problems, such as decreased image quality, image artifacts, incorrect focal spot sizes and/or positions, failed magnetics, X-ray tube damage (e.g., punctures, anode meltdown, aperture overheating, etc.), safety issues (e.g., dosimetric errors leading to overexposure of the patient to radiation), and/or unplanned downtime of the X-ray imaging system for service and repairs.

In typical X-ray imaging systems, a calibration file containing appropriate tube calibration data for an X-ray tube is prepared and shipped to a customer on the tube control unit or a portable storage medium along with the X-ray tube. When a customer replaces the X-ray tube within an imaging system, the customer must obtain a new calibration file (or manually update the existing file) that uniquely corresponds to the new X-ray tube to update the tube control unit. The calibration file (or update) is often distributed in portable storage medium such as compact disks, memory sticks or other storage medium. Such portable storage medium is easily lost, misplaced or inadvertently interchanged with another calibration file or update, causing errors to be introduced or other difficulties in updating calibration information.

Furthermore, in some circumstances, an X-ray tube may be replaced with a third party X-ray tube that is not fully compatible with a given tube control unit in an X-ray imaging system. This incompatibility may result in issues similar to those associated with improper calibration data within a configuration file, discussed above. Furthermore, using incompatible third party X-ray tubes may result in warranty issues for the customer or the manufacturer.

The disclosed X-ray imaging systems may facilitate simple and accurate updating of a calibration file to be used by a tube control unit for controlling the operation of a given X-ray tube. Embodiments also minimize or prevent use of an X-ray tube with a mismatched or incompatible control system (tube control unit). Use of the correct calibration file with a given X-ray tube serves to insure proper, reliable and safe operation of the tube specifically, and the imaging system in general. Embodiments also pertain to the collection of X-ray tube operational data that can be used to generate and forecast tube diagnostics, thereby reducing downtime of the tube and corresponding imaging system.

The disclosed X-ray imaging systems may gather operating parameters may then be used to generate diagnostic information for the X-ray tube, such as end-of-life predictions for the tube itself, and/or for individual components, such as bearings, the emitter, or the anode. The ability to forecast X-ray tube or component life may prevent expensive X-ray tube down time and loss of revenues to the user. It may also allow a user or supplier to order and replace an X-ray tube or a component prior to actual failure.

The disclosed X-ray imaging systems may insure that the calibration file(s) used by a tube control unit is always up-to-date and accurate for a given X-ray tube. Moreover, the process can be automatic and transparent to a user, thereby eliminating the need to manually obtain a correct calibration file for a new tube. This minimizes the mismatching of calibration files to reduce problems associated with decreased image quality, image artifacts, incorrect focal spot sizes and/or positioning, failed magnetics, X-ray tube damage (e.g., punctures, anode meltdown, aperture overheating, etc.) dosimetric errors leading to overexposure of the patient to radiation, and/or downtime of the X-ray imaging system for service and repairs and any other problems associated with use of the wrong calibration file. In addition, the disclosed X-ray imaging systems may validate X-ray tubes with functionally compatible control systems (e.g., tube control units) to avoid mismatches. Moreover, embodiments provide the ability to obtain substantially real time diagnostic information that can be used, among other things, to forecast X-ray tube or component failures and thereby avoid costly downtime.

FIG. 1 is a perspective view of an embodiment of an X-ray imaging system 100 that may be used to acquire image data and process, display, and/or analyze the image data. In some circumstances, the system 100 may be referred to as a computed tomography (CT) or X-ray imaging system. The system 100 is an example of an operating environment where the concepts described in this disclosure may be implemented, but it is not limiting. The concepts described may be implemented in other X-ray imaging systems.

Referring to FIG. 1, the system 100 includes a gantry 112 with an X-ray source assembly 114 that projects X-rays toward a collimator or a detector assembly 118 on an opposite side of the gantry 112. The system 100 may include an actuating table 146 to receive and position a patient 122 or an object to be scanned. The actuating table 146 may move to position a patient 122 to be analyzed by the system 100. Specifically, the actuating table 146 may move the patient 122 at least partially through an opening 148 of the gantry 112 such that X-rays from the X-ray source assembly 114 pass through the patient 122 and are received by the detector assembly 118 to obtain information about the patient 122. The detector assembly 118 may include a plurality of detectors 120 to detect x-rays that pass through the patient 122 positioned on an actuating table 146.

The X-ray source assembly 114 may be operatively coupled to a tube control unit ("TCU") 128. The TCU 128 may be communicatively coupled to a system control unit 126, both of which will be described in further detail below. In general, the system control unit 126 may interface with and control various components of the system 100. In addition, the TCU 128 may interface with the X-ray source assembly 114 so as to provide, for example control signals to the X-ray source assembly 114. By way of example, the control signals provided by the TCU 128 may include signals to control, for example, electron steering magnetics and focusing components in an X-ray tube of the X-ray source assembly 114, as will be described further below. In some configurations, a generator (not shown) may provide, for example, power and/or timing signals to the X-ray source assembly 114.

In the illustrated configuration, the TCU 128 is configured as physically separate from the X-ray source assembly 114. In other configurations, the TCU 128 may be integrated with the X-ray source assembly 114. As shown in FIG. 1, the TCU 128 may be positioned on and coupled to the gantry 112 physically separate from the X-ray source assembly 114. In other configurations, not shown, the TCU 128 may be positioned at other portions of the system 100 or may be integrated with the X-ray source assembly 114.

Figure 2:
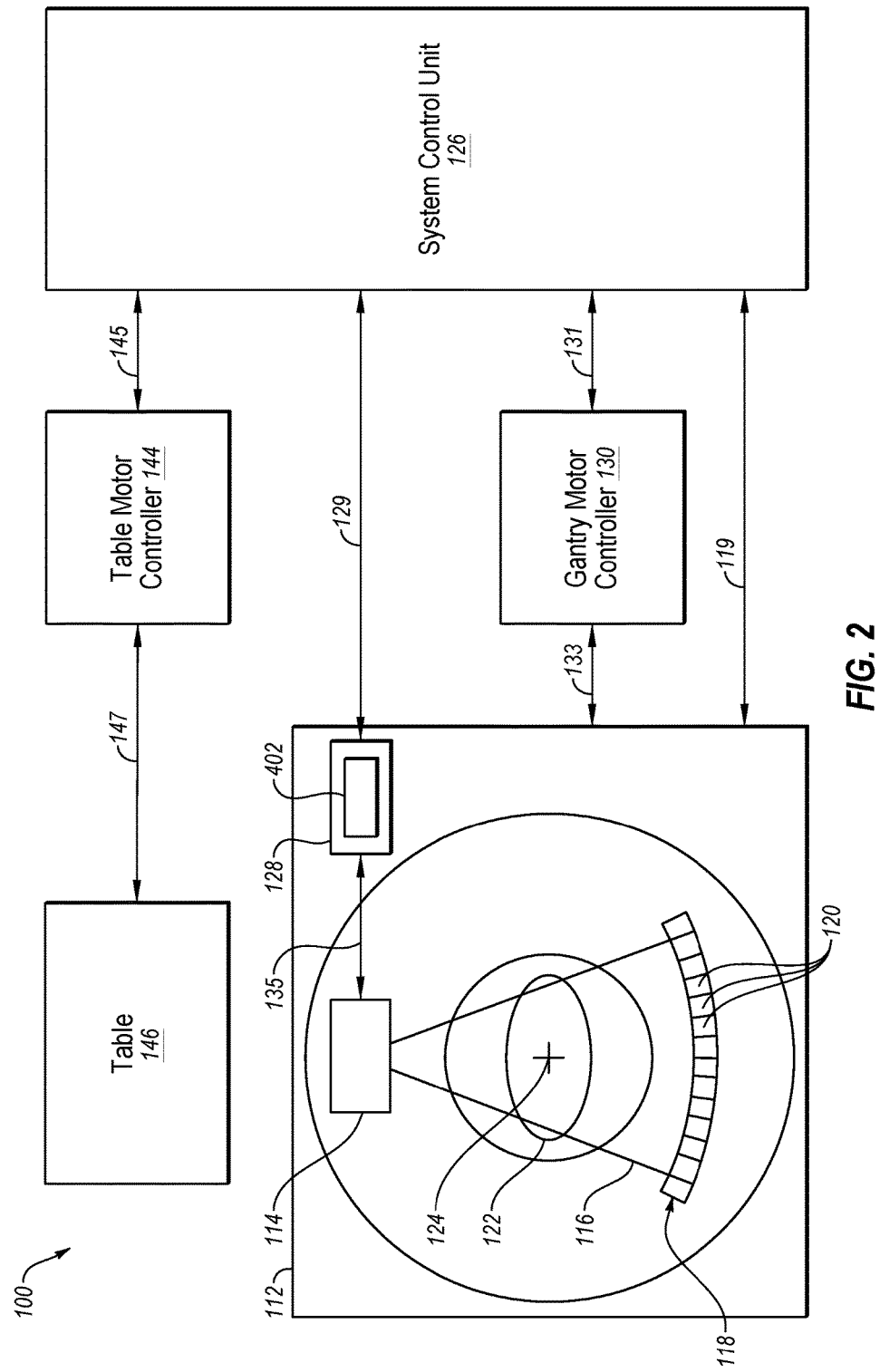
FIG. 2 is a schematic diagram of the X-ray imaging system illustrated in FIG. 1.

FIG. 2 is a schematic diagram of the system 100 illustrated in FIG. 1. The detectors 120 of the detector assembly 118 may produce analog electrical signals that represent the intensity of an impinging X-ray beam 116 and hence the attenuated beam as it passes through the patient 122. As illustrated, the detector assembly 118 may be operatively coupled to the system control unit 126 via an appropriate interface denoted at 119. The analog electrical signals from the detectors 120 may be converted to digital signals and may be transmitted to the system control unit 126.

The system 100 may include a gantry motor controller 130 and a table motor controller 144. The gantry motor controller 130 may control, for example, the rotation, speed, and position of gantry 112 via interface 133, and the table motor controller 144 may control the actuating table 146 via interface 147, to position the patient 122. In the illustrated embodiment, both the gantry motor controller 130 and the table motor controller 144 are operatively coupled to the system control unit 126, as denoted at interface 131 and 145, respectively.

During a scan of the patient 122 to acquire X-ray projection data, the actuating table 146 may position a portion of the patient 122 to be analyzed at least partially through the opening 148 of the gantry 112 during operation (see, for example, FIG. 1), the gantry 112 and the components mounted thereon may rotate about a center of rotation 124, and the X-ray source assembly 114 may emit X-rays, denoted at 116, that travel through the patient 122 to the detector assembly 118.

As noted, the gantry motor controller 130 and the table motor controller 144 may be operatively coupled (denoted at 131 and 145) to the system control unit 126. In this way, rotation of the gantry 112 and actuation of the actuating table 146 may be at least partially controlled by the system control unit 126.

The system control unit 126 may receive the digital signals representative of the radiation received at the detector assembly 118, which may be processed or stored in memory. The system control unit 126 may receive commands and scanning parameters from an operator via a console (not shown) that has some form of operator interface, such as a display, keyboard, mouse, or any other suitable interface components. An associated display (not shown) may allow the operator to observe images and other data from the system control unit 126. The system control unit 126 may be operatively connected to the TCU 128 via an appropriate interface (denoted at 129), and the operator may thus input commands and parameters via the system control unit 126 to provide, for example, control signals to the TCU 128. In a similar fashion, the operator may also make adjustments to the operation of the X-ray assembly 114 via the TCU 128, which is operably interfaced with the X-ray assembly 114, as denoted at 135. For example, the operator may alter focusing and beam steering of the X-ray assembly 114 within specified parameters by providing control parameters to the TCU 128. In some configurations, the operator may make adjustments to the operation a generator (not shown) to provide, for example, power and/or timing signals to the X-ray source assembly 114.

Although the system 100 illustrated is configured to analyze the patient 122, in alternative configurations the system 100 may be configured to analyze a sample or analyte rather than a patient. In such circumstances, the actuating table 146 and/or the gantry 112 may be adapted based on the size and shape of the sample to be analyzed.

Figure 3:
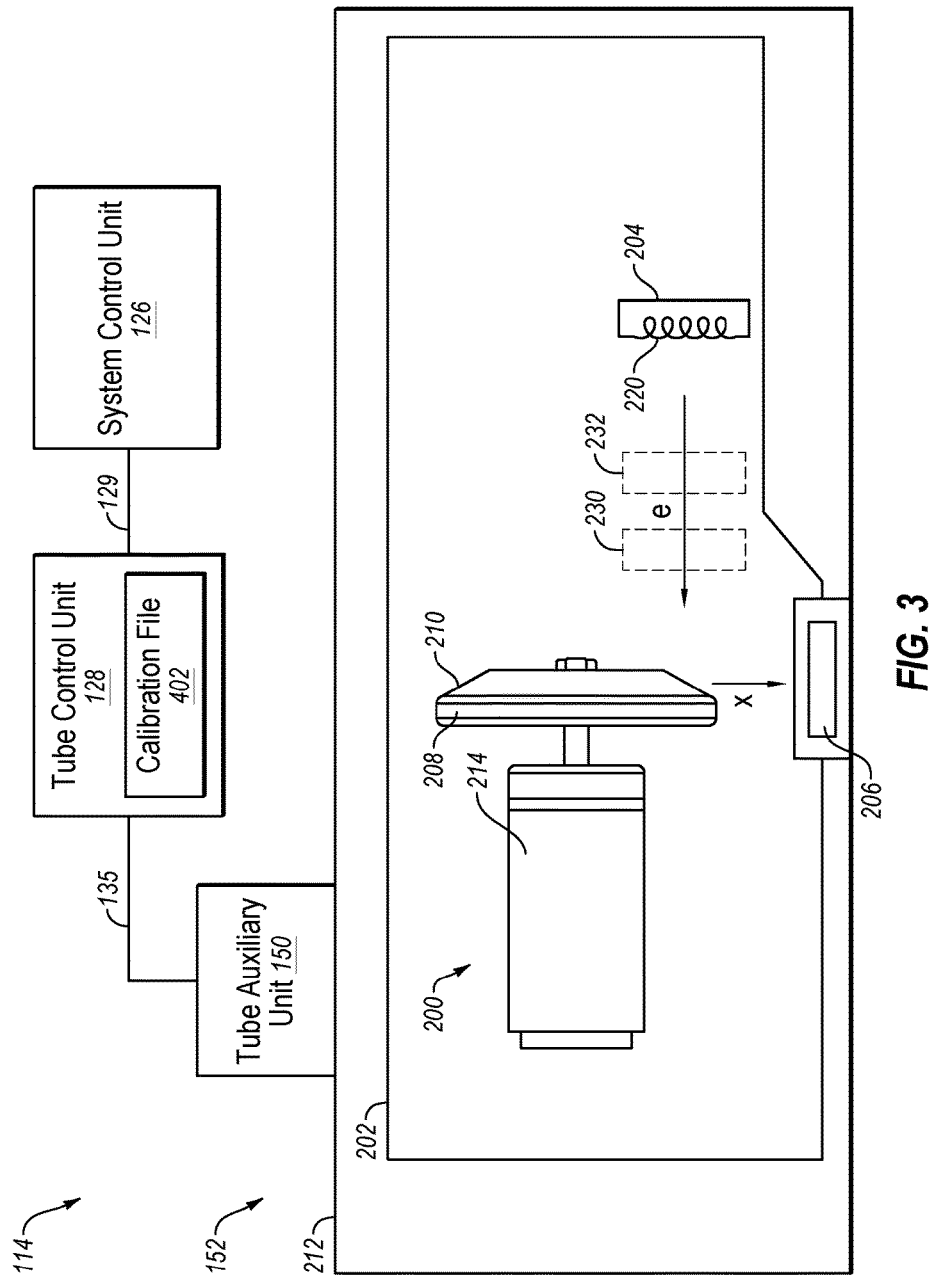
FIG. 3 is a schematic diagram of a portion of the X-ray imaging system illustrated in FIG. 1.

FIG. 3 is a schematic diagram of a portion of the example system 100 illustrating one example of the X-ray source assembly 114 in further detail. The X-ray source assembly 114 includes an X-ray tube 152. In the illustrated configurations, the X-ray tube 152 includes an evacuated enclosure 202 disposed within an outer housing 212. Disposed within the evacuated enclosure 202 is a cathode 204 and an anode assembly 200, which in this embodiment includes a rotating anode 208. In other configurations, the X-ray tube 152 may include other anode configurations, such as a stationary anode.

The anode 208 and cathode 204 are spaced apart from one another and are connected in an electrical circuit that allows for the application of a high voltage potential between them. The cathode 204 includes an electron emitter 220 that is connected to an appropriate power source (e.g., a generator, not shown).

A housing 212 may partially or entirely surround the evacuated enclosure 202. The housing 212 may define or include cooling lines or a cooling chambers (not shown) configured to receive a coolant to manage the temperature of the X-ray tube 152.

During operation of the example X-ray tube 152, an electrical current is supplied to the electron emitter 220 (typically fashioned as a filament) of the cathode. This causes the electrons "e" to be formed on the emitter 220 by thermionic emission. The application of a high voltage differential between the anode 208 and the cathode 204 then causes the electrons "e" to accelerate from the electron emitter 220 toward a focal track 210 that is positioned on the rotating anode 208. The focal track 210 may include, for example, tungsten, rhenium or other material(s) having a high atomic ("high Z") number. As the electrons "e" accelerate, they gain a substantial amount of kinetic energy, and upon striking the rotating focal track 210, some of this kinetic energy is converted into X-rays "x".

The focal track 210 is oriented so that emitted X-rays "x" may pass through a window 206 formed in the evacuated enclosure 202. The window 206 may include an X-ray transmissive material such that the X-rays "x" emitted from the focal track 210 pass through the X-ray tube window 206 and travel to a patient or object. The window 206 may contribute to sealing the vacuum of the evacuated enclosure 202 of the X-ray tube 152 from atmospheric air pressure outside the X-ray tube 152, while permitting X-rays "x" generated by the anode 208 to exit the X-ray tube 152.

As mentioned, the X-ray tube 152 may be a rotating anode type X-ray tube with a rotating anode 208. The anode 208 may be supported by a bearing assembly 214 that permits the anode 208 to rotate. The bearing assembly 214 may include a rotor and bearings (not shown). The rotor may be mechanically coupled to the anode 208 and the bearings may permit the rotor to rotate. A stator (not shown) may induce rotation of the rotor by electromagnetic induction. The stator may be positioned outside of the evacuated enclosure 202 proximate the rotor positioned inside of the evacuated enclosure 202 in a known manner.

With reference to FIGS. 2 and 3, the TCU 128 controls operation of the X-ray tube 152 based on a calibration file 402 that, among other things, provides information to control electron steering magnetics 230 and focusing components 232 (i.e., to control the position and/or size of the electron focal spot). In some configurations, the TCU 128 may apply the calibration file 402 to algorithms stored on the TCU 128 to control the electron steering magnetics 230 and/or the focusing components 232. At least a portion of the calibration file 402 includes data that is specific to the X-ray tube 152 based on the unique operational characteristics of the X-ray tube 152. For example, the calibration file 402 may include focal spot sizes and focal spot positions for various combinations of tube operating voltages (kV) and tube emitter currents (mA) that are unique to the X-ray tube 152. In another example, the calibration file 402 includes electric current magnitude for the steering magnetics 230 and corresponding offsets of the focal spot of the X-ray tube 152. In some configurations, the TCU 128 automatically updates the calibration file 402 based on the data specific to the X-ray tube 152. Examples of a calibration file 402 is described in further detail below.

As shown in FIG. 3, the system 100 may include a tube auxiliary unit ("TAU") 150. The TAU 150 may be communicatively coupled to the TCU 128 such that the TAU 150 and the TCU 128 may transmit and/or receive signals between one another. The TCU 128 may also be communicatively coupled to the system control unit 126. Accordingly, signals or data may be transmitted between the TAU 150, the TCU 128 and the system control unit 126. The TAU 150 may provide the TCU 128 with the data that is specific to the X-ray tube 152 such as tube manufacture data, tube calibration data and/or tube operating data for the calibration file 402, as discussed in further detail below.

With continued reference to FIG. 3, the TAU 150 may be mechanically coupled to the housing 212 of the X-ray tube 152 in a manner such that the TAU 150 is operative during operation of the X-ray tube 152 (e.g., while a patient is being scanned). The TAU 150 may be permanently or semi-permanently (for example, in a manner that permits removal for servicing, replacement, etc.) coupled to the housing 212. In other configurations, the TAU 150 may be positioned at other portions of the X-ray tube 152 or the system 100.

In some embodiments the TAU 150 may be included as an integral part of the X-ray tube 152. In other configurations, the TAU 150 may be a separate component from the X-ray tube 152. In further configurations, the TAU 150 may be included in the TCU 128, or vice versa.

Figure 4:
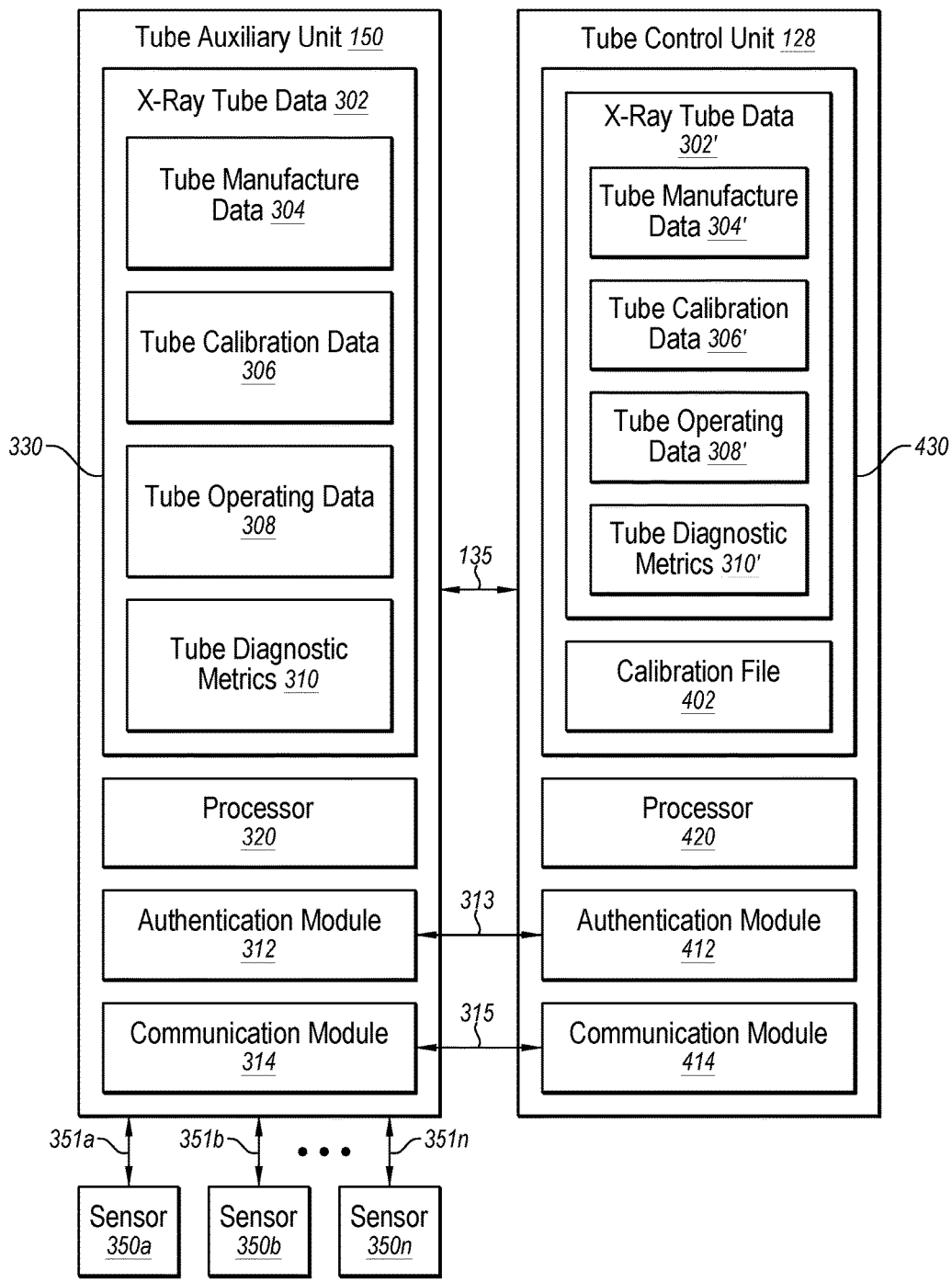
FIG. 4 is another schematic diagram of a portion of the X-ray imaging system illustrated in FIG. 1.

FIG. 4 is a schematic diagram of a portion of the system 100 illustrating example functional aspects of the TAU 150 and the TCU 128. As illustrated, the TAU 150 may include X-ray tube data 302 that is stored in a memory 330. The X-ray tube data 302 may include information unique to the X-ray tube 152. The X-ray tube data 302 may include, for example, tube manufacture data 304, tube calibration data 306 and/or tube operating data 308. The TCU 128 may include tube control unit data, such as the calibration file 402 that is stored in memory 430. The tube control unit data on the calibration file 402 may include focusing and steering calibration data and/or related algorithms, described in further detail below, to control, for example, electron steering components (such as the electron steering magnetics 230) and electron focusing components (such as the focusing components 232) in the X-ray tube 152, and also described in further detail below. The TCU 128 may apply the calibration file 402 to its algorithms for controlling the electron steering magnetics 230 and the electron focusing components 232 of the X-ray tube 152.

The TAU 150 and the TCU 128 may be communicatively coupled to one another, as denoted at 135. For example, the TAU 150 and the TCU 128 may be coupled to send analog, digital and/or wireless signals. In some configurations, the TAU 150 and the TCU 128 may be communicatively coupled via an encrypted link 135 or other suitable secure connection. In other configurations, the TCU 128 may be communicatively coupled to the gantry 112.

The system 100 may be configured to authenticate the TAU 150 and the TCU 128 to ensure they are functionally compatible, as described in further detail below. The authentication may prevent data exchange between X-ray tubes and tube control units that are not functionally compatible. As will be further described, data may be not be transferred between the X-ray tube 152 and the TCU 128 unless the X-ray tube 152 and the TCU 128 are first authenticated to one another. This may prevent inadvertent mismatching between tube and controller.

The tube manufacture data 304 may include information corresponding to the manufacture of the X-ray tube 152. At least some of the tube manufacture data 304 may be unique to the X-ray tube 152, either partially or in the aggregate. By way of example and not limitation, the tube manufacture data 304 may include the unique serial number of the X-ray tube 152, the part number of the X-ray tube 152, the model number of the X-ray tube 152, manufacture date of the X-ray tube 152, the manufacturing location of the X-ray tube 152, the country of origin of the X-ray tube 152, the application code version of the X-ray tube 152, the bootloader version of the X-ray tube 152 and/or other information related to the manufacture of the X-ray tube 152.

The tube calibration data 306 may include information based on testing or calibration parameters of the X-ray tube 152 and that may reflect unique operating characteristics of the X-ray tube 152. Specifically, the tube calibration data 306 may include information obtained during testing of the X-ray tube 152 as part of the manufacturing and set up process. Such tube calibration data 306 may then be included in the TAU 150 after the X-ray tube 152 is manufactured and configured for use by the end user. At least some of the tube calibration data 306 may be unique to the X-ray tube 152, either partially or in the aggregate.

By way of example, the tube calibration data 306 may include a table with focal spot sizes and focal spot positions for various combinations of tube operating voltages (kV) and tube emitter currents (mA). The tube calibration data 306 may also include electric current magnitude for steering magnetics and corresponding offsets of the focal spot of the X-ray tube 152. An example of such a data table that may be included in the tube calibration data 306 is illustrated in Table 1:

TABLE 1

| kV | mA | Focal Spot Size (FS) | Focus 1 | Focus 2 |
|----|----|----|----|----|
| AA | BA | CA | DA | EA |
| AB | BB | CB | DB | EB |
| AC | BC | CC | DC | EC |

In Table 1, focal spot size may be represented either numerically or with letters corresponding to a relative focal spot size. For example, 0 may represent a relatively small focal spot size and 1 may represent a relatively large focal spot size. Other numbers may be used to represent other focal spot sizes, such as medium, extra-large or extra-small focal spot sizes. In another example, the letter "S" may represent a relatively small focal spot size and the letter "L" may represent a relatively large focal spot size. Other letters may be used to represent other focal spot sizes, such as medium, extra-large or extra-small focal spot sizes. Current values for focusing or steering may be also be represented numerically. For example, Table 1 includes numerical values for the current required for various operating conditions. The amount of current required may depend on operating kV, mA, and/or focal spot size. Accordingly, each combination of operating kV, mA, and focal spot size may include two values for current. One of the current values may correspond to an X direction and the other current value may correspond to a Y direction.

In some configurations, the tube calibration data 306 may include multiple tables with different current magnitudes for different kV and/or mA operating settings.

In addition to the above, the focusing and steering calibration data and/or algorithms of the calibration file 402 of the TCU 128 may include steering driver calibration data, focus driver calibration data, steering position calibration data, offset values, fine adjustment values (or user adjustment values), and other tube calibration data. The steering driver calibration data may provide adjustments based on steering driver circuitry (e.g., steering driver board) that is used to control the steering magnetics 230 (see FIG. 3) positioned within the X-ray tube used to impose a magnetic field on the emitted electrons ("e" in FIG. 3). The steering position calibration data may include position data for deflection or steering patterns. The magnetic field alters the direction traveled by the electrons and can thereby be used to "steer" the electrons to a desired position on the focal track 210 of the anode 208. The focus driver calibration data may provide adjustments based on focus driver circuitry or focusing driver circuitry (e.g., focus driver board) that is used to control the relative size and/or shape (focusing) of the electron beam (and the resultant electron focal spot on the focal track 210) by way of the steering components 232 (see FIG. 3) positioned within the X-ray tube.

The TCU 128 may include offset data such as calculated values generated during electron central X-ray beam alignment or focus spot alignment. Fine adjustment values (or user adjustment values) may include additional adjustments or user adjustments in steering (e.g., position correction values) or focusing (e.g., size correction values). The user adjustment values may be a section of the data can be accessed or changed by user control. The changes to user adjustment values may be small or minor and within the safety parameters of the X-ray tube 152. In some configurations, the calibration file 402 (tube control unit data) may include focusing and steering calibration data combined with the X-ray tube data 302 in the TCU 128.

In some configurations, the TCU 128 may include separate tables for information stored on the TCU 128. For example, the TCU 128 may include separate tables such as a focus calibration table, a steering calibration table, a steering pattern table, and/or a custom adjustment table. When the TCU 128 is booted up, the information from the various tables may be combined with the tube calibration data 306 in the calibration file 402. In some embodiments, the calibration file 402 may include a table with combined data. An example of such a data table that may be included in the calibration file 402 is illustrated in Table 2:

TABLE 2

| record | kV | mA | Focal Spot Size(FS) | Focus Coils | | Steering Coils | | | | | | | |
|---|---|---|---|---|---|---|---|---|---|---|---|---|---|
| | | | | | | Position 0 | | Position 1 | | Position 2 | | Position 3 | |
| | | | | Focus 1 | Focus2 | y | x | y | x | y | x | y | x |
| FA | GA | HA | IA | JA | KA | LA | MA | PA | QA | RA | SA | TA | UA |
| FB | GB | HB | IB | JB | KB | LB | MB | PB | QB | RB | SB | TB | UB |
| FC | GC | HC | IC | JC | KC | LC | MC | PC | QC | RC | SC | TC | UC |
| FD | GD | HD | ID | JD | KD | LD | MD | PD | QD | RD | SD | TD | UD |
| FE | GE | HE | IE | JE | KE | LE | ME | PE | QE | RE | SE | TE | UE |

The table of the calibration file 402 may include numerical values for focus calibration from the focus calibration table, steering calibration from the steering calibration table, steering pattern from the steering pattern table, and/or custom adjustments from the custom adjustment table.

The TAU 150 may be configured to log the tube operating data 308. The tube operating data 308 may be obtained from the X-ray tube 152, the TCU 128 or one or more sensors associated with the X-ray tube 152. The tube operating data 308 may be obtained during operation of the X-ray tube 152, either partially or entirely.

The tube operating data 308 may include electrical current of the X-ray tube 152, electrical voltage of the X-ray tube 152, electrical current of the electron emitter 220, electrical current of a motor or a stator, flow rate of coolant, exposure duration, rotational speed of the anode 208, acceleration rate of the anode 208, vibration of the gantry 112, vibration of the X-ray tube 152, speed of the gantry 112, load amount of the gantry 112, pressure of the evacuated enclosure 202 and temperature of at least a portion of the X-ray tube 152.

The system 100 may include one or more sensors 350a, 350b, . . . 350n. At least one of the sensors 350a-350n may include: a timer, a speed sensor, an accelerometer, a position sensor, a temperature sensor, a current sensor, a voltage sensor, a pressure sensor, and a flow sensor, or any combination thereof.

The sensors 350a-350n may be positioned at various positions in the system 100. At least one of the sensors 350a-350n may be part of the TAU 150, the X-ray tube 152, or other components of the system 100. At least one of the sensors 350a-350n may be mechanically coupled to the X-ray tube 152. At least one of the sensors 350a-350n may be mechanically coupled to the housing 212 or positioned at least partially inside of the housing 212 of the X-ray tube 152. At least one of the sensors 350a-350n may be positioned at least partially inside the evacuated enclosure 202. In such configurations, the evacuated enclosure 202 may include an interface that permits the evacuated enclosure 202 to maintain a vacuum seal while permitting the sensor(s) to obtain information and communicate with components of the system 100. Furthermore, in configurations where at least one of the sensors 350a-350n is positioned inside the evacuated enclosure 202, the sensor(s) may wirelessly communicate with components of the system 100.

For example, electrical voltage or voltage potential of the X-ray tube 152 may be measured by a voltage sensor. Electrical current of electron emitter 220 may be measured by an electrical current sensor. Electrical current of a motor or a stator may be measured by an electrical current sensor. Flow rate of coolant may be measured by a flow sensor. Exposure duration may be measured by a timer. Rotational speed of the anode 208 may be measured by a speed sensor. Acceleration rate of the anode 208 may be measured by an acceleration sensor. Relative position of the anode 208 may be measured by a position sensor. Acceleration rate of the anode 208 may be measured by an acceleration sensor. Vibration of the gantry 112 may be measured by a speed sensor or an acceleration sensor. Vibration of the X-ray tube 152 may be measured by a speed sensor or an acceleration sensor. Speed or of the gantry 112 may be measured by a speed sensor. Load amount of the gantry 112 may be measured by an accelerometer or a load sensor positioned. Pressure of the evacuated enclosure 202 may be measured by a pressure sensor. Temperature of at least a portion of the X-ray tube 152 may be measured by a temperature sensor. The temperature sensor may be positioned in any position suitable to measure the temperature of a predetermined region or portion of the X-ray tube 152.

In some configurations, the sensors 350a-350n may be coupled to the TAU 150 via any suitable coupling mechanism, denoted at 351a, 351b, . . . 351n to send signals and/or tube operating data 308. For example, the sensors 350a-350n may be coupled to the TAU 150 to send analog, digital and/or wireless signals. Additionally or alternatively, the sensors 350a-350n may be communicatively to other suitable portions of the system 100 such as the TCU 128 or other computing systems.

The TAU 150 may include an authentication module 312 or device that is operatively connected to the TCU 128. The authentication module 312 may be configured to authenticate the X-ray tube 152 with the TCU 128. The authentication module 312 may include data that indicates whether the TAU 150 or the X-ray tube 152 is functionally matched with the TCU 128. In some configurations, the authentication module 312 may include an ATSHA204A authentication chip produced by Atmel, or another suitable authentication chip or module. In other configurations, the authentication module 312 may be implemented as a field-programmable gate array (FPGA) or a software module. In some configurations, the authentication module 312 may be configured to withstand the operating conditions of the X-ray tube 152. For example, the authentication module 312 may be configured to withstand operating temperatures, pressure, rotational forces and/or other conditions of the X-ray tube 152. In one example, the authentication module 312 may be configured to withstand operating temperatures of at least 40° C., 75° C., and/or 85° C. In another example, the authentication module 312 may be configured to withstand g-forces of at least 22 g or 44 g. In yet another example, the authentication module 312 may be configured to withstand pressures of at least 70 kPa or 106 kPa.

The TAU 150 of the X-ray tube 152 may be configured not to transfer certain data to the TCU 128 before the TCU 128 is authenticated with the TAU 150. Additionally or alternatively, the TCU 128 may be configured not to transfer certain data to the TAU 150 before the TAU 150 is authenticated with the TCU 128. For example, the TAU 150 may be configured to release or transmit the tube manufacture data 304, the tube calibration data 306 and/or the tube operating data 308 to the TCU 128 only after the TCU 128 is validated. Accordingly, the X-ray tube 152 may not be operable until the TCU 128 and the TAU 150 are authenticated with one another. This may prevent an X-ray tube from being operated with a functionally incompatible tube control unit, leading to flawed or potentially dangerous operation of the X-ray tube. In some configurations, the system 100 may only be operational after the TCU 128 and the TAU 150 are authenticated with one another.

The X-ray tube 152 may include a tamper avoidance device associated with the authentication module 312. The tamper avoidance device may be configured to discourage manipulation or prevent unauthorized manipulation of the authentication module 312.

In some configurations, the authentication module 312 may implement an authentication protocol that is compliant with the Advanced Encryption Standard (AES) or the Triple Data Encryption Algorithm (3DES) authentication standard. In other configurations, the authentication module 312 may implement other suitable authentication protocols. The authentication module 312 may be configured to authenticate the TCU 128 based on first authentication data indicating whether the X-ray tube 152 is functionally matched with the TCU 128. The authentication module 312 may be configured to be authenticated by the TCU 128 based on second authentication data indicating whether the TCU 128 is functionally matched with the X-ray tube 152.

The TCU 128 may include an authentication module 412 or device corresponding to the authentication module 312. The authentication module 412 may be operatively coupled to the authentication module 312 of the TAU 150. The authentication module 412 may be configured to authenticate the TCU 128 with the TAU 150. The authentication module 412 may include data that indicates whether the TCU 128 is functionally matched with the TAU 150 or the X-ray tube 152. In some configurations, the authentication module 412 may include an ATSHA204A authentication chip produced by Atmel, or another suitable authentication chip or module. In other configurations, the authentication module 412 may be implemented as a field-programmable gate array (FPGA) or a software module. In some configurations, the authentication module 412 may be configured to withstand the operating conditions of the X-ray tube 152. For example, the authentication module 412 may be configured to withstand operating temperatures, pressure, rotational forces and/or other conditions proximate the X-ray tube 152 and/or on the gantry 112. In one example, the authentication module 412 may be configured to withstand operating temperatures of at least 40° C., 75° C., and/or 85° C. In another example, the authentication module 412 may be configured to withstand g-forces of at least 22 g or 44 g. In yet another example, the authentication module 412 may be configured to withstand pressures of at least 70 kPa or 106 kPa.

The authentication module 312 and the authentication module 412 may be communicatively coupled to one another via any suitable coupling mechanism, denoted at 313 to transmit signals between one another. For example, the authentication module 312 and the authentication module 412 may be coupled to send analog, digital, and/or wireless signals. In some configurations, the authentication module 312 and the authentication module 412 may be communicatively coupled via an encrypted link 313 or other suitable secure connection. The secure connection may be configured to substantially prevent circumvention of the authentication mechanism provided by the authentication module 312 and the authentication module 412.

The TCU 128 may include a tamper avoidance device associated with the authentication module 412. The tamper avoidance device may be configured to discourage manipulation or prevent unauthorized manipulation of the authentication module 412.

In some configurations, power for the TAU 150 may be provided by the X-ray tube 152.

In some configurations, the authentication module 412 may implement an authentication protocol that is compliant with the Advanced Encryption Standard (AES) or the Triple Data Encryption Algorithm (3DES) authentication standard. In other configurations, the authentication module 412 may implement other suitable authentication protocols. The authentication module 412 may be configured to authenticate the TAU 150 based on first authentication data indicating whether the X-ray tube 152 is functionally matched with the TCU 128. The authentication module 412 may be configured to be authenticated by the TCU 128 based on second authentication data indicating whether the X-ray tube 152 is functionally matched with the TCU 128.

The TAU 150 may include memory 330 and/or a processor 320. The memory 330 may log or store the X-ray tube data 302 including the manufacture data 304, the tube calibration data 306 and/or the tube operating data 308. The processor 320 may be configured to generate one or more tube diagnostic metrics 310 based at least in part on the tube operating data 308 obtained by the sensors 350a-350n for the X-ray tube 152. The tube diagnostic metrics 310 may include remaining bearing life, remaining anode life, remaining emitter life and a vacuum failure indicator. In some configurations, the processor 320 may be a microprocessor, field-programmable gate array (FPGA), or similar device or circuit. In some configurations, the processor 320 may be a SAM4E16E, SAM4E8E, SAM4E16C, or SAM4E8C ARM-based Flash MCU produced by Amtel, or another suitable processor. In some configurations, the processor 320 and/or the memory 330 may be configured to withstand the operating conditions of the X-ray tube 152. For example, the processor 320 and/or the memory 330 may be configured to withstand operating temperatures, pressure, rotational forces and/or other conditions of the X-ray tube 152 and/or on the gantry 112. In one example, the processor 320 and/or the memory 330 may be configured to withstand operating temperatures of at least 40° C., 75° C., and/or 85° C. In another example, the processor 320 and/or the memory 330 may be configured to withstand g-forces of at least 22 g or 44 g. In yet another example, the processor 320 and/or the memory 330 may be configured to withstand pressures of at least 70 kPa or 106 kPa.

The TAU 150 may include a communication module 314 to transmit information between the TAU 150 and the TCU 128 over a communication link 315. Additionally or alternatively, the communication module 314 may transmit information between the TAU 150 and a computer system remote from the X-ray tube 152. In some configurations, the communication link 315 may be one or more of: an electrical cable, an optical cable, a local area network connection, a wide area network connection, a Wi-Fi connection, a Bluetooth connection, a cellular connection, or a combination thereof. In other configurations the communication link 315 may be any suitable link to communicatively couple the TAU 150 and a computer system remote from the X-ray tube 152.

In some configurations, the circuitry of the TAU 150 may include electrical protection from the voltage spikes generated by the operation of the X-ray tube 152. For example, the circuitry may include transient-voltage-suppression (TVS) diodes between the power and signal lines and ground. The TVS may be a clamping device that operates by shunting excess current when an induced voltage exceeds an avalanche breakdown voltage thus suppressing overvoltages above a predetermined voltage (e.g., a breakdown voltage). In some configurations, the circuitry of TAU 150 may protect the TAU 150 from voltage dumps of up to, or greater than, 140 kV.

In some configurations, the TAU 150 may be configured to withstand the operating conditions of the X-ray tube 152. For example, the processor 320 and/or the memory 330 may be configured to withstand operating temperatures, pressure, rotational forces and/or other conditions of the X-ray tube 152 and/or on the gantry 112. In some configurations, the TAU 150 may be heat resistant to withstand the operating temperatures of the X-ray tube 152. In one example, the TAU 150 may be configured to withstand operating temperatures of at least 40° C., 75° C., and/or 85° C. In another example, the TAU 150 may be configured to withstand g-forces of at least 22 g or 44 g. In yet another example, the TAU 150 may be configured to withstand pressures of at least 70 kPa or 106 kPa.

The TCU 128 may include memory 430 and/or a processor 420. The memory 430 may store or log the X-ray tube data 302' received from the TAU 150 and/or the sensors 350a-350n. The received X-ray tube data 302' may correspond to or be identical to the X-ray tube data 302 on the TCU 128. The X-ray tube data 302' may include, for example, tube manufacture data 304', tube calibration data 306' and/or tube operating data 308' corresponding to or identical to the tube manufacture data 304, tube calibration data 306 and/or tube operating data 308 on the TAU 150, respectively. The memory 430 may simultaneously include the calibration file 402 (tube control unit data) and the X-ray tube data 302' received from the TAU 150. In some configurations, the calibration file 402 (tube control unit data) may include the X-ray tube data 302' combined in the memory 430.

The processor 420 may be configured to generate one or more of the tube diagnostic metrics 310 based at least in part on the tube operating data 308 for the X-ray tube 152. The tube diagnostic metrics 310 may include end-of-life predictions or forecasts such as remaining bearing life, remaining anode life, remaining emitter life, a vacuum failure indicator and/or other end-of-life predictions. In some configurations, the processor 420 may be a microprocessor, field-programmable gate array (FPGA), or similar device or circuit. In some configurations, the processor 320 may be a SAM4E16E, SAM4E8E, SAM4E16C, or SAM4E8C ARM-based Flash MCU produced by Amtel, or another suitable processor. In some configurations, the processor 420 and/or the memory 430 may be configured to withstand the operating conditions of the gantry 112 and/or proximate the X-ray tube 152. For example, the processor 420 and/or the memory 430 may be configured to withstand operating temperatures, pressure, rotational forces and/or other conditions proximate the X-ray tube 152 and/or on the gantry 112. In one example, the processor 420 and/or the memory 430 may be configured to withstand operating temperatures of at least 40° C., 75° C., and/or 85° C. In another example, the processor 420 and/or the memory 430 may be configured to withstand g-forces of at least 22 g or 44 g. In yet another example, the processor 420 and/or the memory 430 may be configured to withstand pressures of at least 70 kPa or 106 kPa.

The TCU 128 may include a communication module 414 to transmit information between the TAU 150, the system control unit 126, and/or a computer system remote from the X-ray tube 152 via the communication link 315. In some configurations, the communication module 414 may include: an electrical cable, an optical cable, a local area network connection, a wide area network connection, a Wi-Fi connection, a Bluetooth connection, a cellular connection, or a combination thereof. In other configurations, the communication module 414 may include any suitable link to communicatively couple the TCU 128 and a computer system remote from the TCU 128.

The TAU 150 may transmit, via the communication link 135, the manufacture data 304, the tube calibration data 306, the tube operating data 308, and/or the tube diagnostic metrics 310 to the TCU 128 and/or a computer system remote from the X-ray tube 152. In turn, the TCU 128 may transmit, via the communication link 135, the manufacture data 304', the tube calibration data 306', the tube operating data 308', and/or the tube diagnostic metrics 310' to the system control unit 126 and/or a computer system remote from the X-ray tube 152 and/or the TCU 128.

The communication module 314 and the communication module 414 may be communicatively coupled to one another via any suitable coupling mechanism to transmit signals between one another. For example, communication module 314 and the communication module 414 may be coupled by the communication link 315 to send analog, digital, and/or wireless signals. In some configurations, the communication module 314 and the communication module 414 may be communicatively coupled via an encrypted link 315 or other suitable secure connection. In some configurations, the communication links 135, 313, and/or 315 may be a single connection, such as a single encrypted link. In some configurations, the communications links 135, 313, and/or 315 may be separate software layers or communication links of the same physical link.

In a non-illustrated configurations, the system 100 may not include the TCU 128 and the TAU 150 may be communicatively coupled to the system control unit 126. In such configurations, the X-ray tube 152 may be controlled directly by the system control unit 126 and the X-ray tube 152 may not include electron steering magnetics and focusing components. In such configurations, the TAU 150 and the system control unit 126 may be communicatively coupled via an encrypted link or other suitable secure connection, as described herein, for example, with respect to the encrypted link 135. Furthermore, the TAU 150 and the system control unit 126 may perform authentication, validation and/or encryption as described herein with respect to the TAU 150 and the TCU 128. The system 100 may be configured to authenticate the TAU 150 and the system control unit 126 to ensure they are functionally compatible. The authentication may prevent data exchange between X-ray tubes and system control units that are not functionally compatible. Data may be not be transferred between the X-ray tube 152 and the system control unit 126 unless the X-ray tube 152 and the system control unit 126 are first authenticated to one another. This may prevent inadvertent mismatching between tube and the system control unit.

Figure 5:
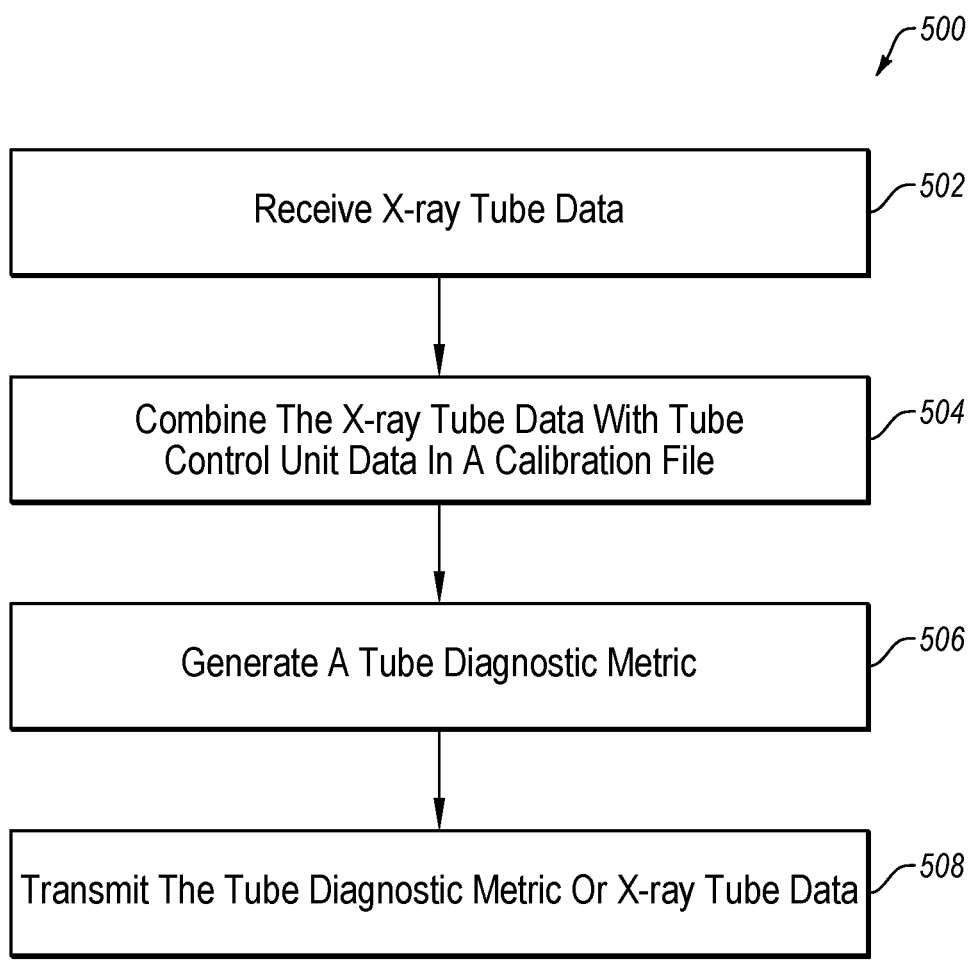
FIG. 5 is a flow chart illustrating an example method.

FIG. 5 is a flow chart of an example method 500, which may be implemented, for example, in the system 100. The method 500 may begin at block 502, in which X-ray tube data may be received at a tube control unit from a tube auxiliary unit. The received X-ray tube data may include tube calibration data, which may reflect unique operating parameters/characteristics of the X-ray tube. In some implementations, the X-ray tube data 302' is received at the TCU 128 from the TAU 150.

At block 504, the X-ray tube data may be combined with tube control unit data in a calibration file. The combined data may be used to create, or otherwise provide the calibration file that is used by the tube control unit to operate at least some aspects of the X-ray tube, including, for example, electron beam control (e.g., electrostatic and/or magnetic focusing and magnetic steering coil settings to control the positioning and size of the electron beam and resulting focal spot provided by the X-ray tube during operation). The method may further include combining the received X-ray tube data with tube control unit data stored at the tube control unit, as well as with any customer adjustment data/parameters.

The calibration file may be stored at the tube control unit. The calibration file may include focusing and steering calibration data to control focusing and steering components of the X-ray tube. In some implementations, the X-ray tube data 302' may be combined with the calibration file 402 (tube control unit data) stored on the memory 430 of the TCU 128.

In some configurations, the X-ray tube data may be encrypted or may include encrypted data. The method 500 may include decrypting the encrypted X-ray tube data. The encrypted X-ray tube data may be decrypted at the tube control unit. In some implementations, the X-ray tube data 302 may be encrypted at the authentication module 312 of the TAU 150. The encrypted X-ray tube data 302' may be received at the TCU 128. The authentication module 412 of the TCU 128 may decrypt the encrypted X-ray tube data 302'. The decrypted X-ray tube data 302' may be stored in the memory 430 of the TCU 128.

In some configurations, the X-ray tube data may include tube operating data obtained during operation of the X-ray tube. At block 506, a tube diagnostic metric may be generated based on the tube operating data. In some implementations, the tube diagnostic metric 310 may be generated based on the tube operating data 308 by the processor 320 of the TAU 150 or the processor 420 of the TCU 128.

At block 508, the tube diagnostic metric or X-ray tube data may be transmitted to a computer system. The tube diagnostic metric or X-ray tube data may be transmitted via a communication link. The computer system may be remote from the tube control unit. In some implementations, the tube diagnostic metric 310 or X-ray tube data 302 may be transmitted to computer system remote from the TCU 128 via the communication link 315.

Figure 6:
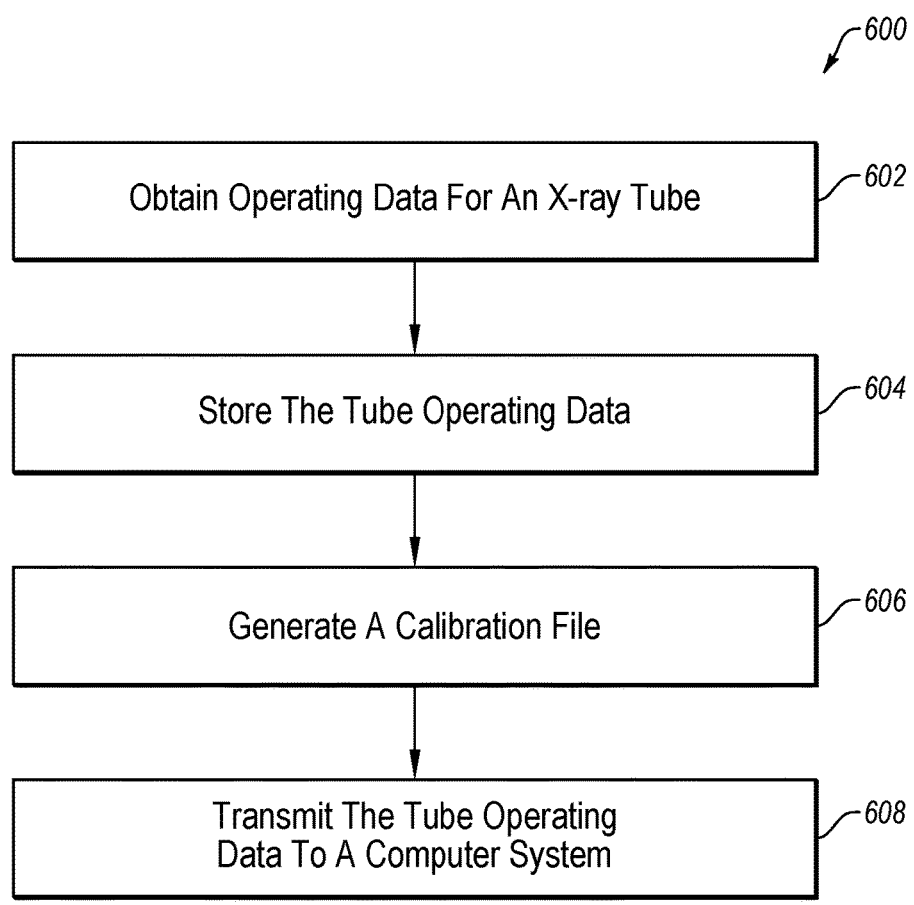
FIG. 6 is a flow chart illustrating another example method.

FIG. 6 is a flow chart of an example method 600, which may be implemented, for example, in the system 100. The method 600 may begin at block 602, in which tube operating data is obtained for an X-ray tube. The tube operating data may be obtained by one or more sensors operatively coupled to the X-ray tube. In some implementations, one or more of the sensors 350a-350n operatively coupled to the X-ray tube 152 may obtain the tube operating data 308 for the X-ray tube 152.

At block 604, the tube operating data may be stored. The tube operating data may be stored in memory of a tube auxiliary unit. In some implementations, the tube operating data 308 may be stored in the memory 430 of the TCU 128.

At block 606, a calibration file may be generated or updated by combining the tube operating data with tube control data. The tube operating data may be combined with the tube control data in a calibration file on the tube control unit. For example, in some implementations, the tube operating data 308 of the X-ray tube data 302 may be combined with the calibration file 402 (tube control unit data) on the memory 430 of the TCU 128.

At block 608, the tube operating data may be transmitted to a computer system. The computer system may be remote from the X-ray tube. In some implementations, the tube operating data 308 may be transmitted from the X-ray tube 152 or the TAU 150 to the TCU 128 and/or a computer system remote from the X-ray tube 152.

In some configurations, the tube operating data may not be transmitted to the TCU 128 before the TCU 128 is authenticated with the TAU 150. For example, the TAU 150 may be configured to release or transmit certain data only after the TCU 128 is validated.

Figure 7:
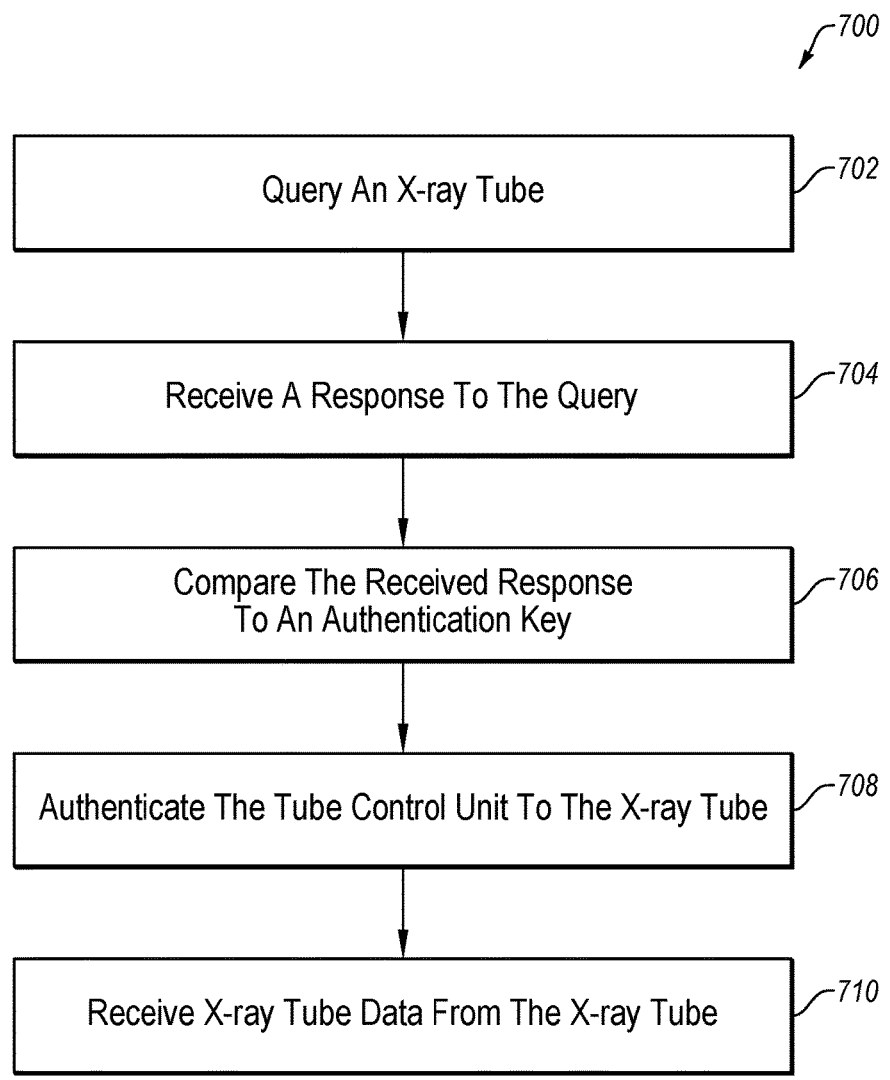
FIG. 7 is a flow chart illustrating another example method.

FIG. 7 is a flow chart of an example method 700, which may be implemented, for example, in the system 100. The method 700 be used to confirm that an X-ray tube is properly matched to a tube control unit to establish that the two devices will interoperate correctly. The method 700 may include, for example, exchanging one or more authentication codes, either from the X-ray tube to the tube control unit, the tube control unit to the X-ray tube, or both (two-way authentication). If the exchanged code(s) match a predetermined key, for example, then it is determined that the X-ray tube and the tube control unit provide an intended match. In some embodiments, only once a match is confirmed between a given tube and tube control unit will the X-ray tube release its calibration data to the tube control unit. In some embodiments, the authentication codes are exchanged via an encrypted communication link. In still further embodiments, authentication codes are continuously changed to prevent unauthorized detection of a code.

The method 700 may begin at block 702, in which an X-ray tube may be queried. The X-ray tube may be communicatively coupled to a tube control unit. The X-ray tube may be queried by the tube control unit. In some implementations, the X-ray tube 152 may be queried by the TCU 128. For example, the authentication module 312 of the X-ray tube 152 may be queried by the authentication module 412 of the TCU 128.

At block 704, a response to the query may be received. The response may be received at the tube control unit from the X-ray tube. In some implementations, the authentication module 412 of the TCU 128 may receive the response to the query from the authentication module 312 of the TAU 150.

At block 706, the received response may be compared to the authentication key. The authentication key may be associated with the tube control unit. The tube control unit may compare the received response to the authentication key. In some implementations, the authentication module 412 of the TCU 128 compare the received response to the authentication key.

At block 708, the tube control unit may be authenticated to the X-ray tube. The tube control unit may be authenticated to the X-ray tube if the authentication key matches the response received from the X-ray tube. The tube control unit may be authenticated to the X-ray tube in response to the received response matching the authentication key. In some implementations, the TCU 128 may be authenticated to the X-ray tube 152 if an authentication key matches a response received from the TAU 150 of the X-ray tube 152.

At block 710, X-ray tube data may be received from the X-ray tube at the tube control unit. The X-ray tube data may be received from the X-ray tube after the authentication of the X-ray tube. In some implementations, the TCU 128 may receive the X-ray tube data 302 after the authentication of the X-ray tube 152 by the authentication module 412 of the TCU 128. In some configurations, the X-ray tube data 302 may be encrypted by the authentication module 312 of the TAU. The encrypted X-ray tube data 302 may be received at the TCU 128. The method 700 may include decrypting the encrypted X-ray tube data 302. In some configurations, X-ray tube data 302 may not be received from the X-ray tube 152 until after the TCU 128 has been authenticated with the TAU 150, or vice versa.

The method 700 may further include receiving an authentication query from the X-ray tube, generating a response to the authentication query; and authenticating the tube control unit to the X-ray tube if a second identification key matches the response. The method 700 may include receiving X-ray tube data from the X-ray tube in response to the X-ray tube authenticating the tube control unit, the X-ray tube data based on parameters of the X-ray tube.

In some configurations of the method 700, the authentication is performed base on first authentication data indicating whether the X-ray tube is functionally matched with the tube control unit. In some configurations of the method 700, the authentication is performed base on second authentication data indicating whether the tube control unit is functionally matched with the X-ray tube.

In some configurations, X-ray tube data may not be received from the X-ray tube at the tube control unit until after the TCU 128 has been authenticated with the TAU 150, or vice versa.

Figure 8:
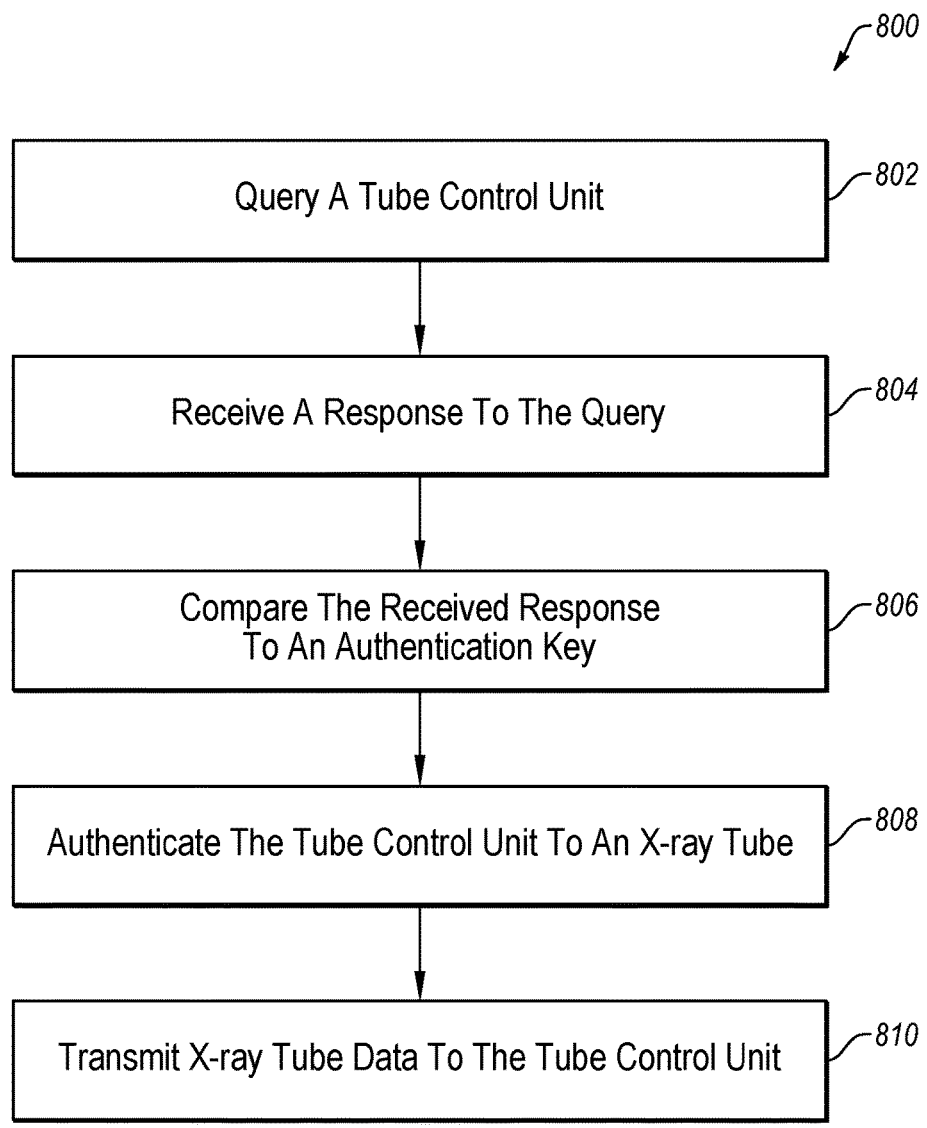
FIG. 8 is a flow chart illustrating another example method.

FIG. 8 is a flow chart of an example method 800, which may be implemented, for example, in the system 100. The method 800 be used to confirm that a tube control unit is properly matched to an X-ray tube to establish that the two devices will interoperate correctly. The method 800 may include, for example, exchanging one or more authentication codes, either from the X-ray tube to the tube control unit, the tube control unit to the X-ray tube, or both (two-way authentication). If the exchanged code(s) match a predetermined key, for example, then it is determined that the X-ray tube and the tube control unit provide an intended match. In some embodiments, only once a match is confirmed between a given X-ray tube and tube control unit will the X-ray tube release its calibration data to the tube control unit. In some embodiments, the authentication codes are exchanged via an encrypted communication link. In still further embodiments, authentication codes are continuously changed to prevent unauthorized detection of a code.

The method 800 may begin at block 802, in which a tube control unit may be queried. The tube control unit may be communicatively coupled to an X-ray tube. The tube control unit may be queried by a tube auxiliary unit of an X-ray tube. In some implementations, the TCU 128 may be queried by the TAU 150 of the X-ray tube 152. For example, the authentication module 412 of the TCU 128 may be queried by the authentication module 312 of the X-ray tube 152.

At block 804, a response to the query may be received. The response may be received at the tube auxiliary unit of the X-ray tube from the tube control unit. In some implementations, the authentication module 312 of the TAU 150 may receive the response to the query from the authentication module 412 of the TCU 128.

At block 806, the received response may be compared to an authentication key. The authentication key may be associated with the tube auxiliary unit of the X-ray tube. The tube auxiliary unit of the X-ray tube may compare the received response to the authentication key. In some implementations, the authentication module 312 of the TAU 150 may compare the received response to the authentication key.

At block 808, the tube control unit may be authenticated to the X-ray tube. The tube control unit may be authenticated to the X-ray tube if the authentication key matches the response received from the tube control unit. The tube control unit may be authenticated to the X-ray tube in response to the received response matching the authentication key. In some implementations, the TCU 128 may be authenticated to the X-ray tube 152 if an authentication key matches a response received from the TCU 128.

At block 810, X-ray tube data may be transmitted from the X-ray tube to the tube control unit. The X-ray tube data may be transmitted from the X-ray tube after the authentication of the X-ray tube. In some implementations, the X-ray tube data 302 may be transmitted from the TAU 150 to the TCU 128 after the authentication module 312 of the TAU 150 authenticates the TCU 128 to the TAU 150. In some configurations, X-ray tube data 302 may not be transmitted from the X-ray tube 152 to the TCU 128 until after the TCU 128 has been authenticated with the TAU 150, or vice versa. In some configurations, the X-ray tube data 302 may be encrypted by the authentication module 312 of the TAU. The encrypted X-ray tube data 302 may be transmitted to the TCU 128. The authentication module 412 of the TCU 128 may decrypt the encrypted X-ray tube data 302.

The method 800 may further include receiving an authentication query from the tube control unit, generating a response to the authentication query; and authenticating the X-ray tube to the tube control unit if a second authentication key matches the response. The method 800 may further include encrypting the tube operating data, transmitting the tube operating data to a tube control unit, and decrypting the encrypted tube operating data at the tube control unit.

In some configurations of the method 800, the authentication is performed based on first authentication data indicating whether the X-ray tube is functionally matched with the tube control unit. In some configurations of the method 800, the authentication is performed based on second authentication data indicating whether the tube control unit is functionally matched with the X-ray tube.

In some configurations, the methods 500, 600, 700, 800 may include calibrating the X-ray tube. Calibrating the X-ray tube may include obtaining calibration information specific to the X-ray tube. The calibration information may be stored on the X-ray tube. Additionally or alternatively, the calibration information may be stored in device history file (DHF). The methods 500, 600, 700, 800 may include retrieving the calibration information from the X-ray tube, for example, at a tube control unit. The calibration information may be used to calibrate the tube control unit. Tube control unit calibration data may be stored, for example, in the DHF. The methods 500, 600, 700, 800 may include performing two way cryptographic authentication to authenticate the X-ray tube and the tube control unit with one another. The methods 500, 600, 700, 800 may include uploading the tube calibration to the tube control unit. The methods 500, 600, 700, 800 may include combining calibration tables of the X-ray tube and the tube control unit.

Although illustrated as discrete blocks, various blocks of methods 500, 600, 700, 800 may be divided into additional blocks, combined into fewer blocks, or eliminated, depending on the desired implementation.

In one example embodiment, an X-ray tube may include a housing, a cathode and an anode positioned at least partially inside of the housing. The cathode and the anode may be spaced apart such that a target surface of the anode is positioned to receive electrons emitted by the cathode. The X-ray tube may include an authentication module configured to authenticate the X-ray tube with a tube control unit that is configured to be operatively connected to the X-ray tube and configured to control steering and focusing components of the X-ray tube.

The X-ray tube may include a tamper avoidance device configured to prevent unauthorized manipulation of the authentication module. The authentication module may implement an authentication protocol that is compliant with at least one of the Advanced Encryption Standard (AES) or the Triple Data Encryption Algorithm (3DES) authentication standard. The authentication module may be configured to authenticate the tube control unit based on first authentication data indicating whether the X-ray tube is functionally matched with the tube control unit. The authentication module may be configured to be authenticated by the tube control unit based on second authentication data indicating whether the tube control unit is functionally matched with the X-ray tube.

The X-ray tube may include or be operatively coupled to one or more sensors to obtain tube operating data for the X-ray tube. The X-ray tube may include a processor configured to generate a tube diagnostic metric based at least in part on the tube operating data for the X-ray tube. The X-ray tube may include a communication link configured to transmit the operating data for the X-ray tube to a computer system that is remote from the X-ray tube. The X-ray tube may include memory configured to store the operating data.

In another example embodiment, a method may include: querying an X-ray tube from a tube control unit; comparing a received response to an authentication key associated with the tube control unit; and authenticating the tube control unit to the X-ray tube if the authentication key matches the response. The method may include receiving X-ray tube data from the X-ray tube after the authenticating of the X-ray tube. In some aspects, the X-ray tube data may include tube calibration data based on tested parameters of the X-ray tube.

The method may include combining the X-ray tube data with tube control unit data stored on the tube control unit. The method may include decrypting the X-ray tube data. The method may include: receiving an authentication query from the X-ray tube; generating a response to the authentication query; and/or authenticating the tube control unit to the X-ray tube if a second identification key matches the response. The method may include receiving X-ray tube data from the X-ray tube in response to the X-ray tube authenticating the tube control unit, the X-ray tube data based on parameters of the X-ray tube.

The terms and words used in the above description and following claims are not limited to the bibliographical meanings, but, are merely used to enable a clear and consistent understanding of the disclosure. It is to be understood that the singular forms "a," "an," and "the" include plural referents unless the context clearly dictates otherwise. Thus, for example, reference to "a component surface" includes reference to one or more of such surfaces.

The embodiments described in this disclosure may include the use of a special purpose or general-purpose computer including various computer hardware or software modules, as discussed in greater detail below.

Embodiments within the scope of this disclosure also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions.

As used herein, the term "module" or "component" can refer to software objects or routines that execute on the computing system. The different components and modules described herein may be implemented as objects or processes that execute on the computing system (e.g., as separate threads). While the system and methods described herein may be implemented in software, implementations in hardware or a combination of software and hardware are also possible and contemplated. In this description, a "computer" or "computer system" may be any suitable computing system as previously defined herein, or any module or combination of modules running on a computing system.

For the processes and/or methods disclosed, the functions performed in the processes and methods may be implemented in differing order as may be indicated by context. Furthermore, the outlined steps and operations are only provided as examples, and some of the steps and operations may be optional, combined into fewer steps and operations, or expanded into additional steps and operations.

This disclosure may sometimes illustrate different components contained within, or connected with, different other components. Such depicted architectures are merely exemplary, and many other architectures can be implemented which achieve the same or similar functionality.

Aspects of the present disclosure may be embodied in other forms without departing from its spirit or essential characteristics. The described aspects are to be considered in all respects illustrative and not restrictive. The claimed subject matter is indicated by the appended claims rather than by the foregoing description. All changes which come within the meaning and range of equivalency of the claims are to be embraced within their scope.

What is claimed is:

1. An X-ray tube comprising:
   a housing;
   a cathode and an anode positioned within the housing, the cathode and the anode spaced apart such that a target surface of the anode is positioned to receive electrons emitted by the cathode; and
   a tube auxiliary unit coupled to the housing, the tube auxiliary unit comprising X-ray tube data including tube calibration data based on parameters of the X-ray tube.

2. The X-ray tube of claim 1, wherein the tube auxiliary unit is permanently coupled to the housing.

3. The X-ray tube of claim 1, the X-ray tube data further comprising tube manufacture data including at least one of: serial number, part number, model number, manufacturing date, manufacturing location, country of origin, application code version, and bootloader version.

4. The X-ray tube of claim 1, wherein the tube calibration data is based on parameters tested during manufacture of the X-ray tube.

5. The X-ray tube of claim 1, wherein the tube auxiliary unit is configured to log tube operating data, wherein at least a portion of the tube operating data is obtained during operation of the X-ray tube.

6. The X-ray tube of claim 5, wherein the tube operating data includes at least one of: X-ray tube electrical current, X-ray tube electrical voltage, emitter electrical current, stator electrical current, coolant flow rate, exposure duration, anode rotational speed, anode rate of acceleration, gantry vibration, X-ray tube vibration, gantry speed, gantry load amount, evacuated enclosure pressure and temperature.

7. The X-ray tube of claim 5, wherein the tube auxiliary unit is further configured to generate, from the tube operating data, a tube diagnostic metric comprising one or more of: an end-of-life prediction, remaining bearing life, remaining anode life, remaining emitter life and a vacuum failure indicator.

8. The X-ray tube of claim 1, the tube auxiliary unit further comprising an authentication module that is operatively connected to a tube control unit configured to control electron beam steering and focusing components of the X-ray tube.

9. The X-ray tube of claim 8, wherein the authentication module is configured to authenticate the X-ray tube with the tube control unit.

10. The X-ray tube of claim 8, wherein the authentication module comprises authentication data, wherein the authentication data indicates whether the X-ray tube or the tube auxiliary unit is functionally matched with the tube control unit.

11. The X-ray tube of claim 1, the tube auxiliary unit operatively connected to one or more of: a timer, a speed sensor, an accelerometer, a position sensor, a temperature sensor, a current sensor, a voltage sensor, a pressure sensor; and a flow sensor.

12. The X-ray tube of claim 1, further comprising a communication link to transmit information between the tube auxiliary unit and a computer system remote from the X-ray tube.

13. A method comprising:
   receiving X-ray tube data at a tube control unit from a tube auxiliary unit, the tube auxiliary unit coupled to a housing of an X-ray tube, wherein the received X-ray tube data comprises tube calibration data; and
   combining the X-ray tube data with tube control unit data stored on the tube control unit, wherein the tube control unit data comprises focusing and steering calibration data to control focusing and steering components of the X-ray tube.

14. The method of claim 13, wherein the received X-ray tube data comprises encrypted data, the method further comprising decrypting, at the tube control unit, the encrypted data.

15. The method of claim 13, further comprising authenticating, at the tube control unit, the X-ray tube.

16. The method of claim 13, further comprising authenticating, at the tube auxiliary unit, the tube control unit.

17. The method of claim 13, the received X-ray tube data further comprising tube operating data obtained during operation of the X-ray tube.

18. The method of claim 17, wherein the tube operating data is obtained by one or more sensors operatively coupled to the tube auxiliary unit, further comprising logging the tube operating data in a memory of the tube auxiliary unit.

19. The method of claim 18, wherein the tube operating data includes at least one of: X-ray tube electrical current, X-ray tube electrical voltage, emitter electrical current, stator electrical current, coolant flow rate, exposure duration, anode rotational speed, anode rate of acceleration, gantry vibration, X-ray tube vibration, gantry speed, gantry load amount, evacuated enclosure pressure and temperature.

20. The method of claim 17, further comprising generating, at the tube control unit, a tube diagnostic metric based on the received tube operating data.

21. The method of claim 20, wherein the tube diagnostic metric comprises one or more of: remaining bearing life, remaining anode life, remaining emitter life and a vacuum failure indicator.

* * * * *